United States Patent [19]

Keller

[11] 4,066,074
[45] Jan. 3, 1978

[54] PROTECTIVE GUARD AND METHOD FOR FORMING AND APPLYING

[76] Inventor: Martin Keller, 13880 Wide Acre Road, Golden, Colo. 80401

[21] Appl. No.: 726,609

[22] Filed: Sept. 27, 1976

[51] Int. Cl.² ............................................. A61F 5/04
[52] U.S. Cl. ................................... 128/89 R; 128/90
[58] Field of Search ..................... 128/89 R, 90, 87 R, 128/165

[56] References Cited

U.S. PATENT DOCUMENTS 3,906,943  9/1975  Arluck ................................... 128/90

OTHER PUBLICATIONS

"Plastic Appliances moulded direct to patient", by J. B. Brennan, The Lancet, 1955, vol. 268, pp. 841–844.
Warm'n Form, Advertisement by Thermo-Mold Medical Products, Inc., Aug. 7, 1974.

Primary Examiner—John D. Yasko
Attorney, Agent, or Firm—Wm. Griffith Edwards

[57] ABSTRACT

A protective guard for areas of the shin bone and other parts of the body comprises a flat plate of thermoplastic material mounted on a strip of wrapping material attached to one side of the plate with a flexible adhesive. The plate is formed to the configuration of the area by first heating it on a flat surface such as that of a hand iron. When heated sufficiently the plate may be bent or molded; a layer of insulating material such as a sock is placed over the area and the heated plate then pressed, using wrapping material, into configuration with the area. When cooled and again rigid the plate retains the shaped configuration and the wrapping is then secured about the leg, for example, to hold the plate over the area to be protected. A quick attaching effect is obtained by use of a wrapping material that clings to itself.

8 Claims, 5 Drawing Figures

PROTECTIVE GUARD AND METHOD FOR FORMING AND APPLYING

My invention relates to protective guards for areas of the body and particularly to an improved rigid guard which may be quickly and easily applied to an injured area of the body such as that at the shin.

Various injuries to the body are such that a rigid protector is desirable to prevent further injury or aggravation of the injury. For example, ski boots sometimes rub against the front of the leg of the skier and cause a sore which is aggravated by further skiing. By providing a rigid guard at the injured area of the shin the skier may continue skiing without further injury. It is desirable that such guard fit comfortably against the leg and that it require a minimum of room within the boot. Furthermore, it is desirable that the guard conform to the configuration of the leg. Various attempts have been made to solve the problem presented by such injuries, but while satisfactory for some applications have not proved to be applicable for all cases. Accordingly, it is an object of my invention to provide an improved rigid guard for protecting injured areas of the body.

It is another object of my invention to provide an improved method for shaping a rigid guard to the configuration of an injured area of the body for protection of that area.

It is a further object of my invention to provide an improved rigid protective guard for shin injuries and the like which is of simple construction and which is easily shaped to the configuration of the injured area of the body.

Briefly, in carrying out the objects of my invention, in one embodiment thereof, a thin rectangular plate of thermoplastic material is attached with a flexible adhesive to a strip of strong light fabric which may be used as an attaching bandage. The plate is shaped to the configuration of the body at the area to be protected by heating the plate on a hand iron, heat lamp, or other device to a temperature of, say, 240° to 250°, fahrenheit. This softens the plate which may then be pressed into the desired configuration. To effect this shaping of the guard, a sock or other insulating layer is placed over the area and the heated plate then placed against the area and by pulling around with wrapping material is pressed into the required shape in which the plate is allowed to cool and thereby is set in the required shape. The plate may then be attached to the body by wrapping it with a strip of fabric which clings to itself or by using a plain fabric and an adhesive tape or other attaching means.

The features of novelty which characterize my invention are pointed out with particularity in the claims appended to and forming a part of this specification. My invention itself, however, both as to its organization and method of application, together with further objects and advantages thereof, may best be understood upon reference to the following description taken in connection with the accompanying drawing in which:

Figure 1:
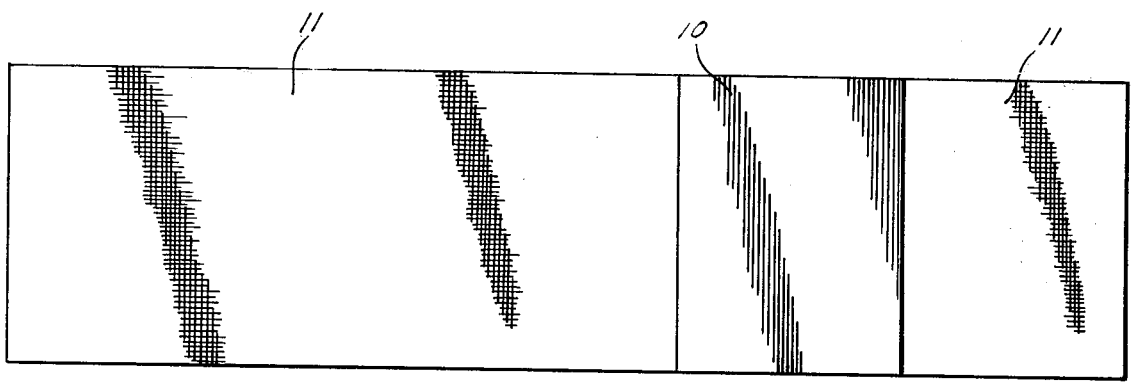
FIG. 1 is a plan view of a guard embodying my invention.
Figure 2:
FIG. 2 is a longitudinal elevation of the guard.

Referring now to the drawing, the guard as shown in FIGS. 1 and 2 comprises a plate 10 of rigid thermoplastic material having a strip 11 of wrapping material attached thereto by flexible adhesive 12. The strip 11 is made of the same width as the plate 10; but may vary if more desirable for some applications. Strip 11 may be a strong gauze like material that clings to itself or it may be another suitable fabric. Other types of attaching element may be used, for example, a teasel element may be attached to one end of the strip and a fleece element to the other, so that the easily attached and detached teasel and fleece may be employed for securing the guard in position.

By way of example, and not by way of limitation, the plate 10 may be made of the acrylic-polyvinyl chloride alloy sheet sold by Rohm and Haas of Philadelphia, Pennsylvania under the trademark KYDEX as KYDEX 100.

The wrapping strip 11 is made of any suitable highly flexible material and may be a gauze, fabric or a webbing material. The strip may be attached to the body by an adhesive tape or the like; also, the gauze or fabric may be of the type which adheres to itself but not to other materials or it may be of a type which adheres to various other materials.

A preferred material for the strip 11 is an elastic gauze bandage such as that sold under the trademark "KLING" by Johnson & Johnson of New Brunswick, New Jersey.

Figure 3:
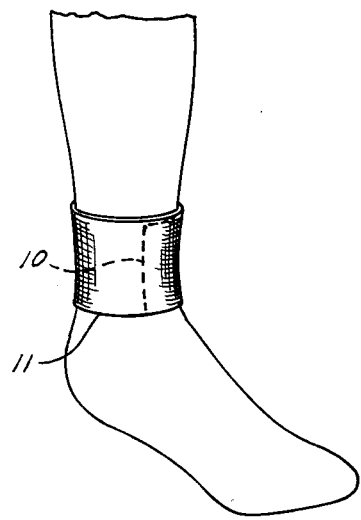
FIG. 3 is a perspective view of the guard as applied to an injured shin.
Figure 4:
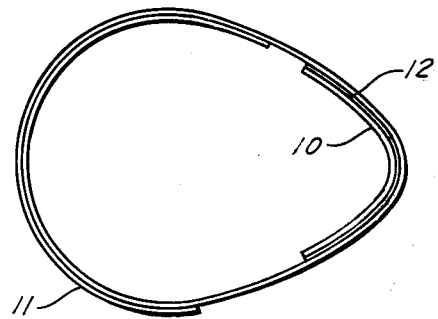
FIG. 4 is a somewhat diagramatic end view of the guard as applied in FIG. 3.
Figure 5:
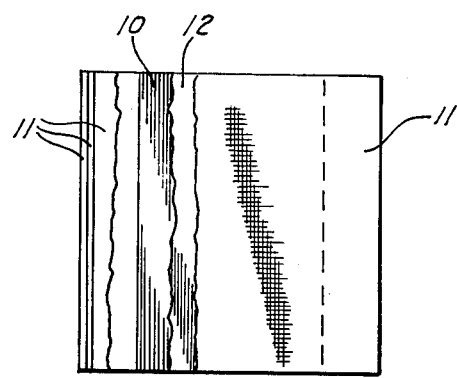
FIG. 5 is a left hand elevation of the guard as shown in FIG. 4 partly broken away.

The manner in which the guard is applied is indicated in FIG. 3 which shows the guard as applied to an injury of the shin. As illustrated the plate 10 has been formed to the configuration of the front of the leg over the shin bone, and the wrapping strip 11 has been placed around the leg and secured.

In order to shape the protective plate a suitable flat heating surface is employed, the face or sole of an electric iron is well suited to the purpose. The iron is first heated to the desired temperature at which the plastic of the plate is moldable; this temperature may, for example, be 250° F. The temperature at which the plastic is moldable may be well above the comfort range for the body and an insulating layer is placed over the skin before pressing the heated plate against it. This layer may, for example, be a medium weight sock; this is particularly suitable for lower leg injuries. The plate is then placed against the sock with the strip 11 on the opposite face and is pressed into position to conform to the leg surface in the area of the injury. The wrapping 11 is then held in position by hand until it has cooled and becomes rigid. It may be left in position or may be removed while the sock is changed or the injury treated. The folded strip may be held over the plate for comfort of the hand at the high initial temperature. The plate 10 may also be heated by a heat lamp or similar radiant heating device, the plate being held in the path of radiation from the heater.

The temperature to which the plate is heated is selected to be sufficiently high that it will not cool below the molding temperature before the plate is molded to the configuration of the area of the body to be protected. The range of temperatures will vary depending upon the characteristics of the plastic of the plate; a range of 240° to 250° F has been found suitable for the plastic identified above.

The attaching of the wrapping 11 to the plate 10 with a flexible adhesive 12 makes it easier to adjust and mold the plate during the forming of the guard because the wrapping is free to expand and contract along with plate 10.

After the plate 10 has been molded and has become rigid again it may be removed and refitted as often as required, it being unnecessary to again heat and mold the plate.

When the guard is supplied to users it is packed with the wrapping strip 11 folded about the plate 10 and a large number of the guards may be packed in a small space. The guard of my invention is inexpensive, easy to use, and provides highly satisfactory individual guards for various different configurations of the body. The arrangement for easily providing a guard conforming to the area of the body to be protected makes a highly effective guard for preventing further injury and for allowing an injury to heal. Thus the guard when applied to a skier' leg makes it comfortable to continue skiing without the annoyance of chafing of the leg by the boot or otherwise injuring the leg.

While the invention has been described in connection with a specific configuration and application of the guard and the method of forming at various other modifications and applications will occur to those skilled in the art. Therefore, I do not desire my invention to be limited to the details illustrated and described and I intend, by the appended claims, to cover all modifications which fall within the spirit and scope of my invention.

I claim:

1. The method for providing a protecting guard for the shin area of the leg which comprises:
    a. providing a thin plate of rigid thermoplastic material with a strip of strong, flexible wrapping material attached to one face thereof, the strip substantially covering the plate and having ends extending substantial distances beyond the plate,
    b. heating the plate to a temperature at which it is sufficiently soft for forming,
    c. placing a layer of soft insulating material over the area to be protected,
    d. pressing the other face of the heated plate against the insulating material to make it conform to the shin area and retaining it in position until it cools and hardens in its bent form,
    e. wrapping the flexible material strip about the leg and bringing the ends into overlapping contact, and
    f. attaching the overlapping strip ends to one another to retain the conformed plate in position over the shin area to be protected.

2. The method of claim 1 wherein said flexible material has the property of adhering to itself and the attaching of said ends is effected by pressing the overlapped ends together.

3. The method of claim 1 wherein the step of pressing the heated plate against the insulated material is effected by pulling the wrapping material around the leg to urge the plate into the required shape over the area to be protected.

4. As an article of manufacture, a guard particularly suited for protecting the shinbone area of the leg comprising a thin flat rigid plate of thermoplastic material having the property of becoming moldable when heated and on cooling becoming rigid again and retaining the shape in which it cools, an elongated strip of strong highly flexible material securely attached to said plate in face engagement with one side thereof, said strip having a width about the same as that of said plate transverse to the strip and having a length sufficient to extend beyond both ends of said plate a distance sufficient for substantial overlapping the ends thereof when the strip is wrapped about a leg with said plate conforming to the shinbone area, and means for utilizing said strip to attach said plate in position over the selected area.

5. An article of manufacture as set forth in claim 4 wherein said strip is attached to said plate with a flexible adhesive on said one face of said plate.

6. An article of manufacture as set forth in claim 4 wherein said plate and said strip are rectangular and said strip is attached to said plate in a manner affording expansion and contraction of the plate and strip together.

7. An article of manufacture as set forth in claim 4 wherein said thermoplastic material becomes moldable within a temperature range of about 240° to 250° F.

8. An article of manufacture as set forth in claim 4 wherein said strip of flexible material has the characteristic of clinging to itself, whereby said ends when overlapped and in engagement hold said plate securely in position.

* * * * *